United States Patent
Zhen et al.

(10) Patent No.: US 12,344,586 B2
(45) Date of Patent: Jul. 1, 2025

(54) PROCESS FOR THE PREPARATION OF BIPHENYLAMINES

(71) Applicant: ADAMA MAKHTESHIM LTD., Beer-Sheva (IL)

(72) Inventors: Xi Zhen, Tianjin (CN); Pingping Tang, Tianjin (CN); Natali Ashush, Bat-Hefer (IL); Einat Kisin-Finfer, Hod Hasharon (IL)

(73) Assignee: ADAMA MAKHTESHIM LTD., Beer-Sheva (IL)

( * ) Notice: Subject to any disclaimer, the term of this patent is extended or adjusted under 35 U.S.C. 154(b) by 651 days.

(21) Appl. No.: 17/628,349

(22) PCT Filed: Jul. 16, 2020

(86) PCT No.: PCT/IL2020/050799
§ 371 (c)(1),
(2) Date: Jan. 19, 2022

(87) PCT Pub. No.: WO2021/014437
PCT Pub. Date: Jan. 28, 2021

(65) Prior Publication Data
US 2022/0380321 A1    Dec. 1, 2022

(30) Foreign Application Priority Data
Jul. 19, 2019 (WO) ............... PCT/CN2019/096684

(51) Int. Cl.
*C07D 241/24* (2006.01)
*C07D 213/82* (2006.01)
*C07D 231/14* (2006.01)

(52) U.S. Cl.
CPC ........ *C07D 241/24* (2013.01); *C07D 213/82* (2013.01); *C07D 231/14* (2013.01); *B01J 2531/824* (2013.01)

(58) Field of Classification Search
CPC .................................................. C07D 241/24
See application file for complete search history.

(56) References Cited

U.S. PATENT DOCUMENTS

| | | | | |
|---|---|---|---|---|
| 6,362,380 B1 * | 3/2002 | Eicken | ............... | C07C 253/30 568/585 |
| 9,868,694 B2 * | 1/2018 | Dockner | ............... | C07F 9/5004 |
| 2008/0183021 A1 | 7/2008 | Engel et al. | | |
| 2014/0323518 A1 | 10/2014 | Cheng et al. | | |

FOREIGN PATENT DOCUMENTS

| WO | 2016094489 A1 | 6/2016 |
|---|---|---|
| WO | 2018035685 A1 | 3/2018 |
| WO | 2018149813 A1 | 8/2018 |

OTHER PUBLICATIONS

Tsang, W.C.P. et al.: "Palladium-Catalyzed Method for the Synthesis of Carbazoles via Tandem C—H Functionalization and C—N Bond Formation". Journal of Organic Chemistry, vol. 73, No. 19, 2008, pp. 7603-7610.

Tsang, W.C.P. et al.: "Palladium-Catalyzed Method for the Synthesis of Carbazoles via Tandem C—H Functionalization and C—N Bond Formation; Supporting Information", Journal of Organic Chemistry, vol. 73, No. 19, 2008, pp. SI-S52.

Asachenko, A.F. et al.: "Suzuki-Miyaura Cross-Coupling under Solvent-Free Conditions", Advanced Synthesis & Catalysis, vol. 355, No. 18, 2013, pp. 3553-3557.

Brocklehurst, C.E. et al.: "Microtiter Plate (MTP) Reaction Screening and Optimization of Surfactant Chemistry: Examples of Suzuki-Miyaura and Buchwald-Hartwig Cross-Couplings in Water", Organic Process Research & Development, vol. 22, No. 10, 2018, pp. 1453-1457.

Jastrzabek, T. et al.: "Suzuki-MiyauraCross-Coupling Towards 4-Amino Biphenyl Intermediates", ChemRxiv. Preprint, Jul. 10, 2019 (Jul. 10, 2019), XP055736620, Retrieved from the Internet: <URL:https://epo.summon.serialssolutions.com/2.0.0/link/0/eLvHCXMwrV3PS8NQDA4rXvSkKPgTevD6uvUltetAxFU3B3rRXjyVlryOouvGZofzrzfpL07mQUvPDXnkNV9Cvi8A5550fSRfKzflAoVkXJV6xDVPI3SahRxEKATn5wjjYfA4xPsWjBsujKknz4wju6NSvvSOafSE2rOfPtbV97G06HJKSflojtVez83cUBSsZLGST4bxiy4SV6RkcnJAosT4ppCxIDAwzYfzWT-USw5Y.

(Continued)

*Primary Examiner* — Golam M Shameem
(74) *Attorney, Agent, or Firm* — FISHERBROYLES, LLP; Roger L. Browdy

(57) ABSTRACT

The invention relates to a method for the preparation of 2-aminobiphenyls, key intermediates in the preparation of compounds of interest in the agrochemical industry. The process comprises reacting an ortho-substituted aniline and a phenylboro derivative in the presence of a base and a palladium catalyst, said palladium catalyst comprising a palladium source and a biphenyl phosphine ligand of formula (III) or a salt thereof.

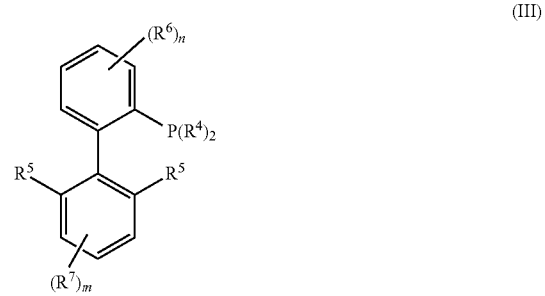

(III)

19 Claims, No Drawings

(56) References Cited

OTHER PUBLICATIONS

Britton, J. et al.: "Synthesis of Celecoxib, Mavacoxib, SC-560, Fluxapyroxad, and Bixafen Enabled by Continuous Flow Reaction Modules", European Journal of Organic Chemistry, vol. 2017, No. 44, 2017, pp. 6566-6574.

Barder, T.E. et al.: Catalysts for Suzuki-Miyaura Coupling Processes: Scope and Studies of the Effect of Ligand Structure, Journal of the American Chemical Society, vol. 127, No. 13, 2005, pp. 4685-4696.

Demchuk, O.M. et al.: "Readily available catalysts for demanding Suzuki-Miyaura couplings under mild conditions", Tetrahedron, vol. 72, No. 42, 2016, pp. 6668-6677.

\* cited by examiner

PROCESS FOR THE PREPARATION OF BIPHENYLAMINES

FIELD OF THE INVENTION

The present invention relates to the field of synthesis of organic compounds, more specifically to a process for the preparation of biphenyl amines, intermediates in the preparation of active ingredients used in the field of agrochemistry.

BACKGROUND PRIOR ART

The agrochemical industry is always in the search of more efficient processes for the preparation of its active ingredients (AIs). The capability of providing economical and clean synthesis of the active ingredients is one of the key factors determining the commercialization of an active ingredient.

Fluxapyroxad, pyraziflumid, bixafen or boscalid are important fungicides. Bixafen was first disclosed in EP 1490342 (Bayer), having the IUPAC name N-(3',4'-dichloro-5-fluoro[1,1'-biphenyl]-2-yl)-3-(difluoromethyl)-1-methyl-1H-pyrazole-4-carboxamide and CAS number 581809-46-3. Fluxapyroxad was first disclosed in EP 1 856 055 (BASF), having the IUPAC name 3-(difluoromethyl)-1-methyl-N-(3',4',5'-trifluoro-[1,1'-biphenyl]-2-yl)-1H-pyrazole-4-carboxamide and CAS number 907204-31-3. Boscalid is disclosed for example in U.S. Pat. No. 5,589,493, having the IUPAC name 2-chloro-N-[2-(4-chlorophenyl)phenyl]pyridine-3-carboxamide and CAS number 188425-85-6. Pyraziflumid is N-[2-(3,4-difluorophenyl)phenyl]-3-(trifluoromethyl)pyrazine-2-carboxamide with CAS number 942515-63-1.

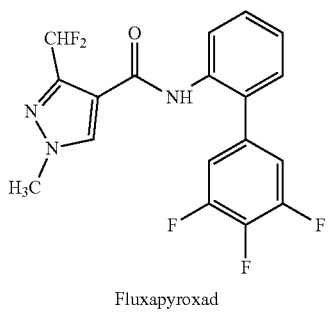

Fluxapyroxad

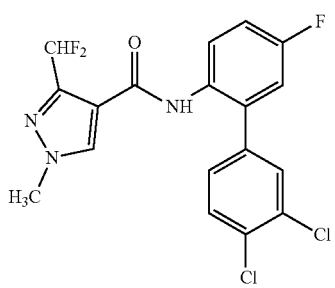

Bixafen

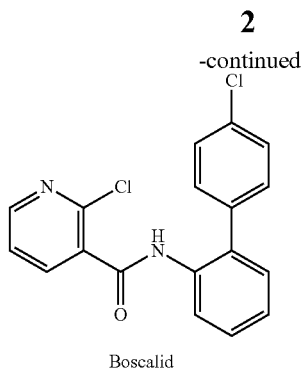

Boscalid

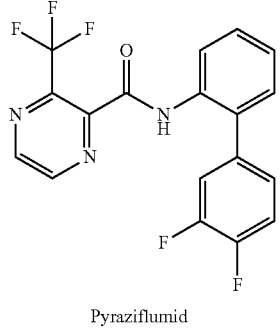

Pyraziflumid

They all belong to the family of the carboxamides and share a substituted ortho-biphenylamine (or ortho-phenylaniline) residue. The most widely used method for preparing these active ingredients involves the condensation of this residue with the carboxy heteroaromatic or aromatic residue. Therefore, the ortho-biphenylamine residues are key intermediates, and any improvement in their synthesis is an important benefit to the overall preparation of the active ingredients.

Consequently, the prior art contains numerous examples of synthesis of these ortho-biphenylamines, namely of 3',4',5'-trifluoro-[1,1'-biphenyl]-2-amine (CAS 915416-45-4), the building block of fluxapyroxad; of 3',4'-dichloro-5-fluoro-2-biphenylamine (CAS 877179-04-9), building block of bixafen; of 4'-chloro-2-biphenylamine (CAS 1204-44-0), building block of boscalid; and of 3',4'-difluoro-2-biphenylamine (CAS 873056-62-3), building block of pyraziflumid.

One strategy involves the coupling of a phenylamine with a phenylhydrazine. For example, WO2013132006 or Heinrich et al, (see "Regioselective Radical Arylation of Anilines with Arylhydrazines", Jasch, Hannelore; Scheumann, Julia; Heinrich, Markus R. *Journal of Organic Chemistry* (2012), 77(23), 10699-10706) disclose the reaction between a phenylamine and 3,4,5-trifluorophenylhydrazine under oxidative conditions, for example, in the presence of manganese dioxide or potassium superoxide. The reaction however suffers of poor regioselectivity and uses reagents such as manganese dioxide or potassium superoxide that are highly contaminant and are thus not suitable for industrial scales.

In US20110301356 a zinc activated trifluorophenyl of formula (III) reacts with a 2-halophenylamine of formula (II) in the presence of a palladium catalyst. However, Zinc metal is very sensitive to moisture and oxidation, and the reaction requires high loadings of Pd catalyst.

Formula of (II) US20110301356

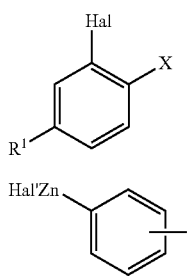

Formula of (III) US20110301356

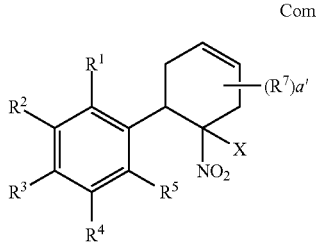

CN107488113 proposes the reaction between an ortho-nitrobenzoic acid and the corresponding halobenzene in the presence of a catalyst. The resulting nitro derivative is then reduced to amine.

Granted U.S. Pat. No. 8,853,455 covers the intermediate 3,4,5-trifluor-2'-nitro-biphenyl. US2011319665 discloses a method for the preparation of the same intermediate that comprises contacting with a base a compound of formula (II) and further aromatization, if required:

Compound (II) of US2011319665

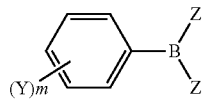

Again, the nitro derivative obtained needs to be reduced to amine in an additional synthetic step.

A common approach for preparing biphenyls is performing a Suzuki-Miyaura coupling between an ortho-halonitrobenzene or an ortho-halophenylamine and a halo-substituted benzene derivative containing a suitable activated group, typically a phenylboronic acid. The reaction typically takes place in the presence of a base and a palladium catalyst comprising a palladium source and a ligand. The resulting nitrobiphenyl product needs to be reduced to amine in an additional synthetic step. Finding a suitable ligand for each family of compounds is one of the key aspects for obtaining good conversion and yields.

JP2013023466 discloses a Suzuki-Miyaura coupling between a compound of formula (II) and compounds of formula (III) in the presence of a palladium catalyst using a nitrogen containing ligand and a second ligand, for example, allylchloro [1,3-bis (2,6-diisopropylphenyl) imidazol-2-ylidene] palladium (II). According to the authors, the product is obtained in good yield without the need of using phosphorous containing ligands nor bromine or iodine.

Formula (II) of JP2013023466

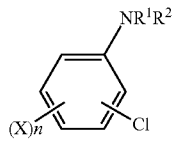

Formula (III) of JP2013023466

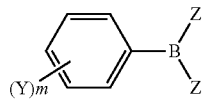

Entry 4 of table 1 provides 3',4',5'-Trifluoro-[1,1'-biphenyl]-2-amine in 99%, using a catalyst loading of 0.05 mol % by using the pre-formed two-ligand catalyst allylchloro [1,3-bis (2,6-diisopropylphenyl) imidazol-2-ylidene] palladium (II).

WO18035685 uses for the Suzuki-Miyaura coupling a ligand of formula (III):

Compound of formula (III) from WO18035685

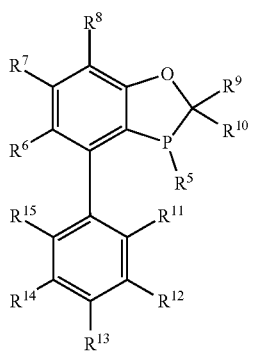

In all the examples the Suzuki-Miyaura coupling is performed between ortho-chloronitrobenzene and 3,4,5-trifluoropehynyl)boronic acid. The resulting nitro compound is then reduced to amine.

US2011105766 uses for the Suzuki-Miyaura coupling a bi-dentate ligand of formula III:

Formula III of US2011105766

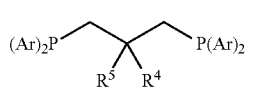

WO2015011032 uses for the Suzuki-Miyaura coupling a ligand of formula (V):

Compound of formula (V) of WO2015011032

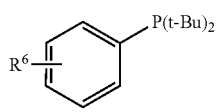

WO 2018/149813 discloses the coupling of an ortho-chloronitrobenzene of formula (II) with a compound of formula (IV) to provide the corresponding nitrobiphenyl of formula (I), which can then be reduced to the corresponding amine in an additional synthetic step.

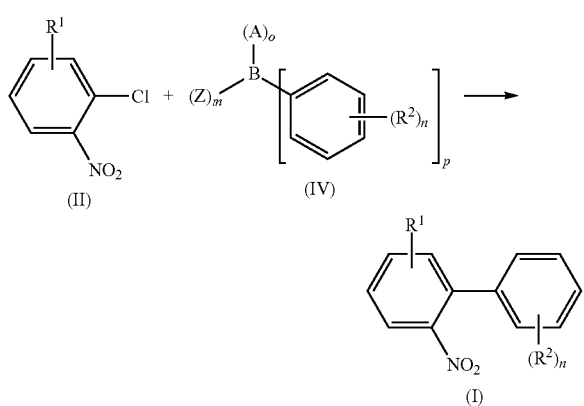

The ligands used are of formula (III); $(R^3)(R^4)ArP$, wherein Ar can be an optionally substituted $C_6$-$C_{10}$ aryl group, typically di-tertbutylphenylphosphines.

There is therefore in the art a need to provide alternative procedures for obtaining biphenyl amines, key intermediates to compounds of interest in the agrochemical industry.

SUMMARY OF THE INVENTION

The inventors have now realized that biphenyl phosphine ligands in combination with a palladium source provide a suitable catalyst for the Suzuki-Miyaura reaction between ortho-substituted anilines and phenylboro derivatives, to yield ortho-biphenylamines.

Thus, a firsts, aspect of the invention is a process to prepare a compound of formula (IV) or a salt thereof

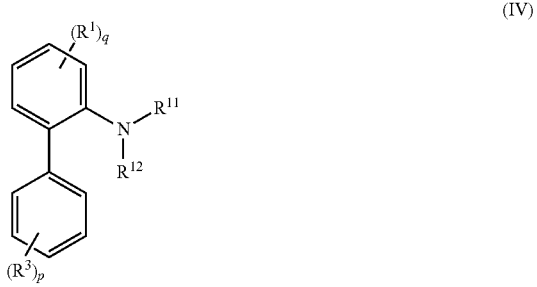

wherein
  q is an integer selected from the group consisting of 0, 1, 2, 3 and 4;
  p is an integer selected from the group consisting of 0, 1, 2, 3, 4 and 5;
  provided that at least one of p or q is 1 or more;
  each of $R^{11}$ and $R^{12}$ is independently selected from hydrogen and a nitrogen protecting group, or $R^{11}$ and $R^{12}$ together form a cyclic nitrogen protecting group;
  each $R^1$ is independently selected from the group consisting of halogen, —OH, $C_1$-$C_6$-alkyl, cyano, $C_1$-$C_6$-haloalkyl, $C_1$-$C_6$-alcoxyl, and $C_1$-$C_6$-haloalcoxyl; and
  each $R^3$ is independently selected from the group consisting of halogen, —OH, $C_1$-$C_6$-alkyl, cyano, $C_1$-$C_6$-haloalkyl, $C_1$-$C_6$-alcoxyl and $C_1$-$C_6$-haloalcoxyl;
the process comprising reacting an ortho-substituted aniline and a phenylboro derivative in the presence of a base and a palladium catalyst, said palladium catalyst comprising a palladium source and a biphenyl phosphine ligand,
wherein said ortho-substituted aniline is a compound of formula (I), or a salt thereof

wherein
  q, $R^1$, $R^{11}$ and $R^{12}$ are as defined above; and
  $X^1$ is a group capable of transmetalation with palladium;
wherein said phenylboro derivative is a compound of formula (II)

wherein
  p and $R^3$ are as defined above;
  y is an integer selected from 0 or 1;
    wherein,
    when y is 1, then z is an integer selected from 1, 2 or 3;
    when y is 0, then z is an integer selected from 1, 2, 3 or 4, and the compound of formula (II) forms a borate accompanied by a cation A having a charge a+;
  and
  each $R^2$ is independently selected from the group consisting of hydrogen, halogen, —OH, —$OR^9$, and $C_1$-$C_{10}$-alkyl, wherein $R^9$ is $C_1$-$C_{10}$-alkyl or $C_6$-$C_{12}$-aryl; or wherein, z being 1, two $R^2$ groups together form a bridging group —O—$(CH_2)_r$—O—, wherein r is 2 or 3, so that said two $R^2$ groups, together with the oxygen atoms and the boron atom, form a 5- or 6-membered ring, where the $CH_2$ groups are optionally substituted by one or two $C_1$-$C_4$-alkyl groups;
and
wherein the biphenyl phosphine ligand is a compound of formula (III) or a salt thereof

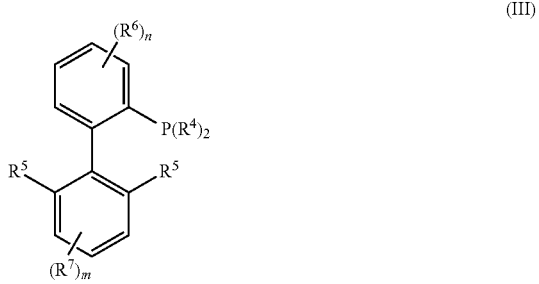

wherein
  m is an integer selected from the group consisting of 0, 1, 2 and 3;
  n is an integer selected from the group consisting of 0, 1, 2, 3 and 4;
  each $R^4$ is independently selected from the group consisting of $C_1$-$C_{16}$-alkyl, $C_3$-$C_{15}$-cycloalkyl, and $C_6$-$C_{10}$-aryl;
  each $R^5$ is independently selected from the group consisting of hydrogen, —$OR^{10}$, —$SR^{10}$, —$N(R^{10})(R^{10})$ $C_1$-$C_{16}$-alkyl, $C_3$-$C_{10}$-cycloalkyl, halogen, cyano, and $C_1$-$C_6$-haloalkyl, provided that one $R^5$ is not hydrogen, wherein $R^{10}$ is selected from the group consisting of $C_1$-$C_{16}$-alkyl, $C_3$-$C_{10}$-cycloalkyl, and $C_1$-$C_6$-haloalkyl;
  each $R^6$ is independently selected from the group consisting of halogen, cyano, $C_1$-$C_6$-alkyl, $C_1$-$C_6$-haloalkyl, $C_1$-$C_6$-alcoxyl and $C_1$-$C_6$-haloalcoxyl;
each $R^7$ is independently selected from the group consisting of halogen, cyano, $C_1$-$C_6$-alkyl, $C_1$-$C_6$-haloalkyl, $C_1$-$C_6$-alcoxyl and $C_1$-$C_6$-haloalcoxyl.

A preferred embodiment of the invention is a process to prepare a compound of Formula (IVA) or a salt thereof

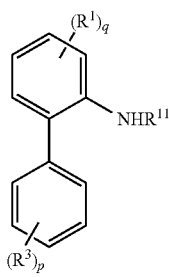

(IVA)

wherein
  q is an integer selected from the group consisting of 0, 1, 2, 3 and 4;
  p is an integer selected from the group consisting of 1, 2, 3, 4 and 5;
  wherein the sum of q and p is 2 or more;
  $R^{11}$ is selected from hydrogen or a nitrogen protecting group;
  each $R^1$ is independently a halogen; and
  each of $R^3$ is independently selected from the group consisting of halogen, —OH, $C_1$-$C_6$-alkyl, cyano, $C_1$-$C_6$-haloalkyl, $C_1$-$C_6$-alcoxyl and $C_1$-$C_6$-haloalcoxyl;
the process comprising reacting an ortho-substituted aniline and a phenylboro derivative in the presence of a base and a palladium catalyst, said palladium catalyst comprising a palladium source and a biphenyl phosphine ligand,
wherein said ortho-substituted aniline is a compound of formula (IA), or a salt thereof

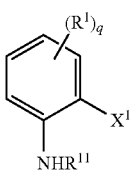

(IA)

wherein
  q, $R^{11}$ and $R^1$ are as defined above; and
  $X^1$ is a group capable of transmetalation with palladium;
wherein said phenylboro derivative is a compound of formula (II)

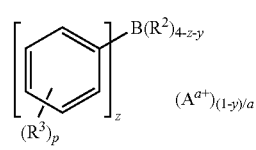

(II)

wherein
  p and $R^3$ are as defined above;
  y is an integer selected from 0 or 1;
    wherein,
    when y is 1, then z is an integer selected from 1, 2 or 3;
    when y is 0, then z is an integer selected from 1, 2, 3 or 4, and the compound of formula (II) forms a borate accompanied by a cation A having a charge a+;
  and
  each $R^2$ is independently selected from the group consisting of hydrogen, halogen, —OH, —$OR^9$, and $C_1$-$C_{10}$-alkyl, wherein $R^9$ is $C_1$-$C_{10}$-alkyl or $C_6$-$C_{12}$-aryl; or wherein, z being 1, two $R^2$ groups together form a bridging group —O—$(CH_2)_r$—O—, wherein r is 2 or 3, so that said two $R^2$ groups, together with the oxygen atoms and the boron atom, form a 5- or 6-membered ring, where the $CH_2$ groups are optionally substituted by one or two $C_1$-$C_4$-alkyl groups;
and
wherein the biphenyl phosphine ligand is a compound of formula (III) or a salt thereof

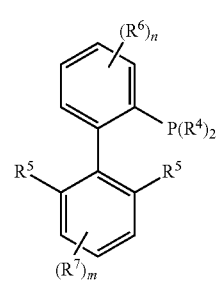

(III)

wherein
  m is an integer selected from the group consisting of 0, 1, 2 and 3;
  n is an integer selected from the group consisting of 0, 1, 2, 3 and 4;
  each $R^4$ is independently selected from the group consisting of $C_1$-$C_{16}$-alkyl, $C_3$-$C_{15}$-cycloalkyl, $C_6$-$C_{10}$-aryl;
  each $R^5$ is independently selected from the group consisting of hydrogen, —$OR^{10}$, —$SR^{10}$, —$N(R^{10})(R^{10})$ $C_1$-$C_{16}$-alkyl, $C_3$-$C_{10}$ cycloalkyl, halogen, cyano, and $C_1$-$C_6$-haloalkyl, provided that one $R^5$ is not hydrogen; wherein $R^{10}$ is selected from the group consisting of $C_1$-$C_{16}$-alkyl, $C_3$-$C_{10}$-cycloalkyl, and $C_1$-$C_6$-haloalkyl;
  each $R^6$ is independently selected from the group consisting of halogen, cyano, $C_1$-$C_6$-alkyl, $C_1$-$C_6$-haloalkyl, $C_1$-$C_6$-alcoxyl and $C_1$-$C_6$-haloalcoxyl; and each $R^7$ is independently selected from the group consisting of halogen, cyano, $C_1$-$C_6$-alkyl, $C_1$-$C_6$-haloalkyl, $C_1$-$C_6$-alcoxyl and $C_1$-$C_6$-haloalcoxyl.

Considering the literature, it was surprising that ligands such as 2-dicyclohexylphosphino-2',6'-dimethoxybiphenyl (SPhos) or 2-dicyclohexylphosphino-2',4',6'-triisopropylbiphenyl (XPhos), developed by Buchwald et al., would provide excellent yields, considering that the reaction involves the coupling of an ortho-activated aniline of formula (I). The literature does not teach Suzuki-Miyaura couplings involving these types of starting materials and it was impossible to predict the behavior of this family of products. Butchwald et al ("Catalysts for Suzuki-Miyaura Coupling Processes: Scope and Studies of the Effect of Ligand Structure" Barder, T. E.; Walker, S. D.; Martinelli, J. R.; Butchwald, S. L. *J. Am. Chem. Soc*, 2005, 127, 4685-4696) discloses the use of 2-(2',6'-dimethoxybiphenyl)dicyclohexyl-phosphine (SPhos) as ligands in the Suzuki-Miyaura reaction for the preparation of biphenyl compounds. According to Butchwald et al, the reaction between 4-chloroaniline and 2,4-difluoropehnylboronic acid proceeds in excellent yield (entry 4, Table 6). On the other hand, recent investigations (Jastrzabek, Tomasz; Ulikowski, Artur; Lisiak, Rafat (2019): Suzuki-Miyaura Cross-Coupling Towards 4-Amino Biphenyl Intermediates. ChemRxiv. Preprint.—http://doi.org/10.26434/chemrxiv.8850296.v1) have tested the reaction between 4-chloroaniline and 3,4,5-trifluoropehnylboronic acid, resulting in a disappointing yield of 42%. Thus, it was not clear how 4-chloroanilines would behave when using biphenyl phosphine ligands, nor was there any information as to the behavior of 2-chloroanilines (or other suitable ortho-activated anilines).

The results where specially surprising in the case of couplings involving highly substituted phenyl rings. In the same paper, Buchwald et al. taught that, even though some fluoro-substituted phenylboronic acids provided good yields (entries 1, 2, 3, and 5, Table 6), the yields were disappointing when using 2,6-difluoro or 2,4,6-trifluoro-phenylboronic acids.

The process of the invention provides a more efficient synthesis of formula (IV) or salts thereof, useful intermediates to compounds of interest such as boscalid, pyraziflumid, fluxapyroxad or bixafen. Thus, a third aspect of the invention is a process to produce a compound of formula (V), or a salt thereof,

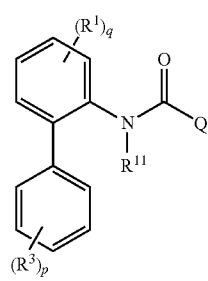

wherein
q is an integer selected from the group consisting of 0, 1, 2, 3 and 4;
p is an integer selected from the group consisting of 0, 1, 2, 3, 4 and 5;
provided that at least one of p or q is 1 or more;
$R^{11}$ is selected from hydrogen or a nitrogen protecting group;
Q is $C_6$-$C_{15}$-aryl or $C_3$-$C_{15}$-heteroaryl, optionally substituted with one or more groups selected from the group consisting of halogen, $C_1$-$C_4$-alkyl and $C_1$-$C_4$-haloalkyl;
each $R^1$ is independently selected from the group consisting of halogen, —OH, $C_1$-$C_6$-alkyl, cyano, $C_1$-$C_6$-haloalkyl, $C_1$-$C_6$-alcoxyl, and $C_1$-$C_6$-haloalcoxyl; and
each $R^3$ is independently selected from the group consisting of halogen, —OH, $C_1$-$C_6$-alkyl, cyano, $C_1$-$C_6$-haloalkyl, $C_1$-$C_6$-alcoxyl and $C_1$-$C_6$-haloalcoxyl;
the process comprising the reaction between an ortho-substituted aniline of formula (I), or a salt thereof

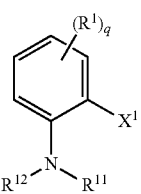

wherein
q and $R^1$ are as defined above; and
$X^1$ is a group capable of transmetalation with palladium;
$R^{11}$ is as defined above;
$R^{12}$ is selected from hydrogen and a nitrogen protecting group;
and a phenylboro derivative of formula (II)

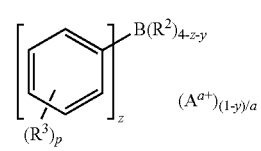

wherein
p and $R^3$ are as defined above;
y is an integer selected from 0 or 1;
wherein,
when y is 1, then z is an integer selected from 1, 2 or 3;
when y is 0, then z is an integer selected from 1, 2, 3 or 4, and the compound of formula (II) forms a borate accompanied by a cation A having a charge a+;
and
each $R^2$ is independently selected from the group consisting of hydrogen, halogen, —OH, —$OR^9$, and $C_1$-$C_{10}$-alkyl, wherein $R^9$ is $C_1$-$C_{10}$-alkyl or $C_6$-$C_{12}$-aryl; or wherein, z being 1, two $R^2$ groups together form a bridging group —O—$(CH_2)_r$—O—, wherein r is 2 or 3, so that said two $R^2$ groups, together with the oxygen atoms and the boron atom, form a 5- or 6-membered ring, where the $CH_2$ groups are optionally substituted by one or two $C_1$-$C_4$-alkyl groups;
in the presence of a base and palladium catalyst, the palladium catalyst comprising a palladium source and a biphenyl phosphine ligand of formula (III) or a salt thereof

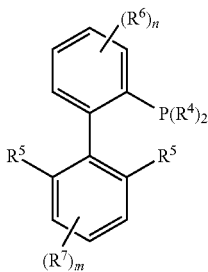

(III)

wherein
m is an integer selected from the group consisting of 0, 1, 2 and 3;
n is an integer selected from the group consisting of 0, 1, 2, 3 and 4;
each $R^4$ is independently selected from the group consisting of $C_1$-$C_{16}$-alkyl, $C_3$-$C_{15}$-cycloalkyl, $C_6$-$C_{10}$-aryl;
each $R^5$ is independently selected from the group consisting of hydrogen, —$OR^{10}$, —$SR^{10}$, —$N(R^{10})(R^{10})$, $C_1$-$C_{16}$-alkyl, $C_3$-$C_{10}$-cycloalkyl, halogen, cyano, and $C_1$-$C_6$-haloalkyl, provided that one $R^5$ is not hydrogen; wherein each $R^{10}$ is independently selected from the group consisting of $C_1$-$C_{16}$-alkyl, $C_3$-$C_{10}$-cycloalkyl, $C_1$-$C_6$-haloalkyl, and $C_1$-$C_6$-alcoxyl;
each $R^6$ is independently selected from the group consisting of halogen, cyano, $C_1$-$C_6$-alkyl, $C_1$-$C_6$-haloalkyl, $C_1$-$C_6$-alcoxyl and $C_1$-$C_6$-haloalcoxyl; and
each $R^7$ is independently selected from the group consisting of halogen, cyano, $C_1$-$C_6$-alkyl, $C_1$-$C_6$-haloalkyl, $C_1$-$C_6$-alcoxyl and $C_1$-$C_6$-haloalcoxyl;
to provide a compound of formula (IV) or a salt thereof

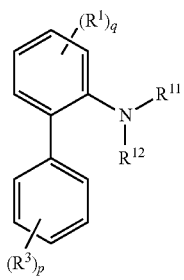

(IV)

wherein
$R^1$, $R^3$, $R^{11}$, $R^{12}$, q, q and p are defined above;
the process further comprising,
if required, obtaining a compound of formula (IV) wherein at least one of $R^{11}$ or $R^{12}$ is hydrogen;
and
reacting a compound of formula (IV) wherein at least one of $R^{11}$ or $R^{12}$ is hydrogen, or a salt thereof, with a compound of formula (VI)

Q-C(=O)—Z      formula (VI)

wherein
Q is a defined above; and
—C(=O)—Z is an acyl precursor.
A fourth aspect of the invention is the use of a compound of formula (III) in the preparation of a compound of formula (IV), or a salt thereof.

A fifth aspect of the invention is the use of a compound of formula (III) in the preparation of a compound of formula (V), or a salt thereof.

DETAILED DESCRIPTION OF THE INVENTION

Definitions

In the present document the following terms are given the meaning below.

"Halogen" refers in the present document to —F, —Cl, —Br or —I.

"Alkyl" means in the present document a straight or branched hydrocarbon chain radical consisting of carbon and hydrogen atoms, containing no unsaturation, having the number of carbon atoms indicated in each case, for example 1-16 carbon atoms ($C_1$-$C_{16}$—), which is attached to the rest of the molecule through a single bond. For example, an alkyl group comprises 1-8 carbon atoms, typically 1-4 carbon atoms. Exemplary alkyl groups can be methyl, ethyl, n-propyl, i-propyl, n-butyl, t-butyl, or n-pentyl.

"Haloalkyl" refers in the present document to an alkyl group that comprises one or more halogen substituents, that is, substituted with at least one of —F, —Cl, —Br or —I. The skilled person is aware of different substituents used frequently in organic chemistry, such as haloalkyl groups comprising 1, 2, 3, 4, 5, 6, 7 or 8 halogen substituents. Haloalkyl groups wherein all positions have been substituted with halogen atoms are also known, for example, perfluoro or perchloro substituents. Exemplary haloalkyl groups can be —$CH_2F$, —$CH_2Cl$, —$CHF_2$, —$CF_3$, —$CCl_3$, or —$CF_2CF_3$.

"Cycloalkyl" means in the present document an alkyl group forming a closed ring and attached to the rest of the molecule through a single bond. Cycloalkyl groups can be substituted with other alkyl groups or form more than one ring. Exemplary cycloalkyl groups can be cyclopropyl, 2-methylcyclopropyl, cyclobutyl, cyclopentyl, cyclohexyl, 2-mehtylcyclohexyl, 4-mehtylcyclohexyl, cycloheptyl or cyclooctyl.

"Cyano" means in the present document —CN.

"Alcoxyl" means in the present document a radical of the formula —O-alkyl, wherein alkyl has been previously defined. Exemplary alkoxyl groups are methoxy, ethoxy or propoxy.

"Haloalcoxyl" refers in the present document to a radical of the formula —O-haloalkyl, for example —O—$CH_2F$, —O—$CH_2Cl$, —O—$CHF_2$, —O—$CF_3$, —O—$CCl_3$, —O—$CF_2CF_3$.

"Aryl" means in the present document an aromatic hydrocarbon radical having the number of carbon atoms indicated in each case, such as phenyl or naphthyl. The aryl radical may be optionally substituted by one, two or three groups selected from the group consisting of halogens, $C_1$-$C_6$-alkyl and $C_1$-$C_6$-haloalkyl groups.

"Aralkyl" means in the present document an aryl group linked to the rest of the molecule through an alkyl group such as benzyl and phenethyl.

"Heteroaryl" means in the present document a stable 3- to 15-membered cycloalkyl ring system attached to the rest of the molecule through a single bond, wherein one to five carbons atoms of the ring scaffold are replaced by heteroatoms selected from the group consisting of nitrogen, oxygen, and sulphur, and wherein at least one of the rings is aromatic. For the purposes of this invention, the heteroaryl may be for example a monocyclic, bicyclic or tricyclic ring system, which may include fused ring systems; and the nitrogen, carbon or sulphur atoms in the heteroaryl radical may be optionally oxidised; the nitrogen atom may be optionally quaternized.

For example, an heteroaryl group can comprise a 4- to 8-membered ring with one or more heteroatoms, for example a 5- or 6-membered ring, wherein one, two or three carbons atoms of the ring scaffold are replaced by heteroatoms selected from the group consisting of nitrogen, oxygen, and sulphur, and wherein at least one of the rings is aromatic. Examples of such heteroaryl groups include, but are not limited to pyridine, pyrazole, benzimidazole, benzothiazole, furan, isothiazole, imidazole, indole, purine, quinoline, thiadiazole.

"Nitrogen protecting group" refers in the present document to a group that blocks an amino group function towards one or more subsequent reactions and that, once said subsequent reactions have taken place, it can be removed under controlled conditions. The amino protecting groups are well known in the art, representative protecting groups are:

acyls of formula —C(=O)R', such as acetate, benzoate. Pivalate, methoxyacetate, chloroacetate or levulinate; carbamates of formula —C(=O)—O—R', such as benzyl carbamate, p-nitrobenzyl carbamate, tert-butyl carbamate, 2,2,2-trichloroethyl carbamate, 2-(trimethylsilyl) ethyl carbamate, allyl carbamate.

In all the above formula R' represents a group selected from the group consisting of alkyl, aryl and aralkyl. Also, different alkyl moieties such as those defined above for R' may be used as amino protecting groups. Additional examples of amino protecting groups can be found in reference books such as Greene and Wuts' "Protective Groups in Organic Synthesis", John Wiley & Sons, Inc., New York, 4th Ed., 2007.

The term "borate" refers to tetrahedral boron anions.

Were indicated, the invention also provides salts of the compounds. For instance, salts of compounds provided herein may be acid addition salts, base addition salts or metallic salts, and they can be synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, non-aqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, ammonium, and organic alkali salts such as, for example, ethylenediamine, ethanolamine, N,N-dialkylenethanolamine, triethanolamine, glucamine and basic aminoacids salts. Examples of the metallic salts include, for example, sodium, potassium, calcium, magnesium, aluminium and lithium salts.

The compounds of the invention are also meant to include compounds which differ only in the presence of one or more isotopically enriched atoms. For example, compounds having the present structures except for the replacement of a hydrogen by a deuterium or tritium, or the replacement of a carbon by a $^{13}C$- or $^{14}C$-enriched carbon, or $^{15}N$-enriched nitrogen, or $^{19}F$ enriched fluorine are within the scope of this invention.

Palladium Catalyst

The inventors have found that the compounds of formula (III) are good ligands promoting the coupling of the compounds of formula (I) and of formula (II).

The compounds of formula (III) were developed by Buchwald et al. and reported in, for example, U.S. Pat. No. 6,395,916 B1 or EP 1 581 467 B1 or in "Catalysts for Suzuki-Miyaura Coupling Processes: Scope and Studies of the Effect of Ligand Structure" Barder, T. E.; Walker, S. D.; Martinelli, J. R.; Butchwald, S. L. *J. Am. Chem. Soc,* 2005, 127, 4685-4696. These and other publications of Buchwald and other authors teach general methods for the preparation of the compounds of formula (III); see for example Buchwald, S. L. et al *J. Am. Chem. Soc.,* 2005, 127, 4685-4696 (scheme 1 on page 4686), or Tomori et al. *J. Org. Chem.,* 2000, 65, 5334-5341.

Different variants are commercially available, for example 2-dicyclohexylphosphino-2',6'-dimethoxybiphenyl (SPhos), 2-dicyclohexylphosphino-2',4',6'-triisopropylbiphenyl (XPhos), 2-dicyclohexylphosphino-2'-methylbiphenyl (MePhos), 2-dicyclohexylphosphino-2',6'-diisopropoxybiphenyl (RuPhos) or 2-(dicyclohexylphosphino)-3,6-dimethoxy-2',4',6'-triisopropyl-1,1'-biphenyl (BrettPhos). SPhos or XPhos are preferred ligands.

In the compounds of formula (III) both $R^4$ groups are typically a cycloalkyl or a heteroaryl, although more frequently $R^4$ is a $C_5$-$C_{15}$-cycloalkyl, for example cyclopentyl, cyclohexyl, cycloheptyl or cyclooctyl, preferably cyclohexyl.

It has been shown in the prior art that a critical feature of the compounds of formula (III) is that at least one of $R^5$ is not hydrogen, preferably both $R^5$ being different from hydrogen, for example, selected from $C_1$-$C_6$ alkyl and $C_1$-$C_6$-alcoxyl, or independently selected from the group consisting of —$OR^{10}$, —$SR^{10}$, —$N(R^{10})(R^{10})$, and $C_1$-$C_{16}$-alkyl; wherein $R^{10}$ is selected from the group consisting of $C_1$-$C_{16}$-alkyl, $C_3$-$C_{10}$-cycloalkyl, and $C_1$-$C_6$-haloalkyl. $R^5$ groups can be the same. Alternatively, one $R^5$ can be hydrogen and the other $R^5$ can be selected from the group consisting of $C_1$-$C_6$ alkyl and $C_1$-$C_6$-alcoxyl.

Thus, it is preferred that n is 0 and/or m is 0 or 1. One of such combinations is a compound of formula (III) wherein m is 1, and $R^7$ is a $C_1$-$C_6$ alkyl. Another possible combination is one wherein n is 1, $R^6$ is selected from $C_1$-$C_6$-alkyl and $C_1$-$C_6$-alcoxyl, m is 1 and $R^7$ is selected from $C_1$-$C_6$-alkyl and $C_1$-$C_6$-alcoxyl.

The palladium catalyst of the invention provides excellent yields and at the same time it is simpler to produce than other catalysts described in the literature for preparing the same compounds. For example the catalyst allylchloro(1,3-bis(2,6-diisopropylphenyl)imidazol-2-ylidene) palladium (II) taught in JP2013023466 requires the use of two different ligands to prepare the catalyst.

The palladium source can be a palladium(II) salt, a palladium complex with ligands different from the ligand of formula (III) or its salts, or it is metallic palladium which is optionally bound to a carrier. Suitable Pd(II) salts are for example Pd(II) acetate, $Na_2PdCl_4$ or $PdCl_2$, preferably Pd(II) acetate or $PdCl_2$. The carrier can be activated carbon, aluminum oxide, barium carbonate, barium sulfate, calcium carbonate, aluminum silicates such as 50 montmorillonite or silica ($SiO_2$), in each case typically having a palladium content of 0.5 to 12% by weight, with respect to the total weight of the palladium source. Besides palladium and the carrier, these catalysts may contain doping substances, for example lead. In case that a Pd(II) salt or a Pd(II) complex is used, Pd(II) is reduced to Pd(0) before the Suzuki reaction starts. The reduction generally takes place in situ.

The palladium catalyst can be formed in situ by adding separately the palladium source and a biphenyl phosphine ligand of formula (III) or a salt thereof into the reaction mixture, or it can be pre-formed and then added to the reaction medium. For practical reasons the palladium catalyst is typically formed in situ. This reduces the number of steps of the process, and in the present case provides satisfactory results, which was not necessarily true for the processes disclosed in the literature or the catalysts commercially available. For example, trying to prepare in situ a PEPPSI™-IPr catalyst ([1,3-Bis(2,6-Diisopropylphenyl)imidazol-2-ylidene](3-chloropyridyl)palladium(II) dichloride), similar to the catalyst allylchloro(1,3-bis(2,6-diisopropylphenyl)imidazol-2-ylidene) palladium (II) disclosed in JP2013023466, provides a significantly less active complex that requires high catalyst loadings. However, the process of the invention can proceed by first forming the palladium catalyst (addition of palladium source and the ligand of formula (III)), while maintaining a catalyst loading from 0.001 mol % to less than 1 mol %, preferably from 0.01 mol % to 0.09 mol %, preferably from 0.01 mol % to less than 0.05 mol %, relative to the amounts of the compound of formula (I). This in situ formation of the catalyst typically takes less than 60 minutes (e.g. 1 to 30 minutes) and proceeds at a temperature comprised between 0° C. and 100° C., preferably between 10° C. and 50° C., more preferably between 15° C. and 30° C.

Thus, the process of the invention preferably comprises a first step of forming the palladium catalysts by contacting the palladium source and a biphenyl phosphine ligand of formula (III), or a salt thereof, followed by contacting the palladium catalyst so formed with the ortho-substituted aniline of formula (I), or a salt thereof, and the phenylboro derivative of formula (II), in the presence of a base. Alternatively, the process of the invention may comprise first contacting the base, the ortho-substituted aniline of formula (I), or a salt thereof, and the phenylboro derivative of formula (II), and then adding the catalyst components.

Typically, the equivalent ratio palladium source:ligand of formula (III) is between 5:1 to 1:5, more preferably from 4:1 to 1:4, even more preferably from 3:1 to 1:4, in particular from 1:1 to 1:4, specifically from 1:1 to 1:3.5.

There is no particular limitation as to the content of the Pd source or the preformed Pd complex (calculated on the basis of the Pd content). Large amounts will produce very fast reactions but will be uneconomical due to the cost of the Pd source, and can create mixtures in which the catalyst is difficult to remove. Too small amounts can result in slow reactions. The Pd source is typically up to 5 mol %, e.g. of from 0.0001 mol % to 5 mol %, relative to the amount of the compound of formula (I). The inventors have found that the Pd source can be added in quite small amounts, for example, from 0.0001 mol % to 2 mol %, more preferably from 0.001 mol % to 1 mol %, in particular from 0.001 mol % to 0.5 mol % or from 0.001 mol % to 0.4 mol %, and specifically from 0.001 mol % to 0.1 mol %, very specifically from 0.002 mol % to 0.06 mol %, or from 0.002 mol % to 0.05 mol %, for example, from 0.01 mol % to less than 0.05 mol %, relative to the amounts of the compound of formula (I).

Compounds of Formula (I)

The compounds of formula (I) are anilines substituted in the ortho position with an $X^1$ group, which is one capable of transmetalation with palladium. These groups are known in the art and are typically —Cl, —Br, —I or —OSO$_2$R$^8$, wherein R$^8$ is $C_1$-$C_{16}$-alkyl, $C_1$-$C_{16}$-haloalkyl or $C_6$-$C_{16}$-aryl optionally substituted with a $C_1$-$C_6$-alkyl group, for example, triflate (—OSO$_2$CF$_3$), mesylate (—OSO$_2$Me), tosylate (—OSO$_2$tolyl) or —OSO$_2$phenyl. It is preferable that $X^1$ is —Cl or —Br. Chlorine is often used when possible; however, it is sometimes necessary to use more reactive groups, such as bromine. One of the advantages of the present process over other prior art documents, such as in CN105384691A or Driver et al (*J. Org. Chem.* 2009, 74, 8, 3225-3228), is the possibility of using the less expensive chloroanilines in the reaction, despite the fact they are less reactive than bromoanilines and other activated anilines.

These ortho-substituted anilines used as starting materials are known in the art and can be purchased or prepared according to known processes. For example, ortho-chloroaniline, ortho-bromoaniline, 2-bromo-3-methyl-aniline, 2-bromo-5-methyl-aniline, 2-bromo-6-methyl-aniline, or 4-amino-3-chlorobenzonitrile are commercially available (e.g. Sigma-Aldrich).

For example, q in the compounds of formula (I) or in the compounds of formula (IA), and the resulting compounds of formula (IV) and formula (IVA) can be 0 or 1. Each $R^1$, when present, in the compounds of formula (I) or in the compounds of formula (IA), and the resulting compounds of formula (IV) and formula (IVA) can be independently selected from a $C_1$-$C_4$-alkyl or a halogen, preferable from a halogen, for example fluor. For example, all R1 can be a halogen, for example fluor or chloro. For example, q can be 0 or, alternatively, q is 1 and each $R^1$ can be fluor or —OH.

The amine of the aniline can be free (i.e. —NH$_2$) or can be protected through groups $R^{11}$ and/or $R^{12}$ representing each a nitrogen protecting group as defined in this document, or can both be connected forming a cyclic nitrogen protecting group. These protecting groups can be later removed once the coupling reaction has taken place. The Suzuki-Miyaura coupling of the invention takes place in excellent yield with the free amine, and it is thus preferred that either $R^{11}$ or $R^{12}$ are hydrogen (for example, as in a compound of formula (IA)), and even more preferred that both $R^{11}$ and $R^{12}$ are each hydrogen. That is, the reaction of the present invention proceeds in excellent yield using compounds of formula (I) wherein both $R^{11}$ and $R^{12}$ are each hydrogen, or of formula (IA) wherein $R^{11}$ is hydrogen.

Preferred compounds of formula (I) used in the process of the invention are ortho-chloroaniline, 5-fluoro-2-chloroaniline, 4-fluoro-2-chloroaniline, 4-hydroxy-2-chloroaniline.

Compounds of Formula (II) and (IV)

The compounds of formula (II) are the phenylboro derivatives necessary for the Suzuki-Miyaura coupling. The preparation of compounds of formula (II) is known to the skilled person, and it is discussed for example in WO 2018/035685 A1 (for example in pages 20 to 25) or in US2018/0093942 A1 (page 4).

When preparing the compounds of formula (II) it must be taken into account that it is frequent to obtain mixtures of different species of compounds of formula (II). For example, a boronic acid (i.e. a compound of formula (II) wherein y is 1 and all R$^2$ groups are —OH), will typically be a mixture of species wherein z is 1, 2 and 3 in different proportions.

In the compounds of formula (II) z can be 1, 2 or 3 when y is 1, thus defining the number of phenyl groups attached to the boron group. For example, the compounds of formula (II) wherein y is 1, typically comprise species wherein z is 1, preferably defining a boronic acid (both R$^2$ are —OH) or a derivative thereof (both R$^2$ are each independently selected from a —OR$^9$). This boronic acids can come in mixtures with the corresponding compounds of formula (II) wherein z is 2 or 3. It is thus preferred that all R$^2$ groups of the compound of formula (II) are —OH. It should also be taken into consideration that such compounds can form trimers.

In another alternative, when y is 1, z can also be 1 and at least one of the two $R^2$ groups is a $C_1$-$C_4$-alkyl group. In another alternative, y is 0, the boron atom being tetrasubstituted and thus forming a borate salt wherein z can be 1 to 4, preferably 1 or 4.

Were a borate salt is formed (y is 0), the counter cation A can be any of the commonly used, for example, an alkali or earth alkaline metal cation or an ammonium cation, for example, an ammonium cation of formula $+N(R^a)(R^b)(R^c)(R^d)$, wherein each of $R^a$, $R^b$, $R^c$ and $R^d$ is independently selected from hydrogen and a $C_1$-$C_6$-alkyl optionally substituted with one or two hydroxyl groups. A is preferably an alkaline metal cation.

Thus, the reaction of the compounds of formula (I) with the compounds of formula (II) in the presence of a palladium catalyst and a base provides the compounds of formula (IV), which are key intermediates in the synthesis of active ingredients used in agriculture. These active ingredients have similar structures, containing one or more halogen substituents. Accordingly, it is preferred that each $R^1$ and each $R^3$ is independently selected from a halogen, preferably from chloro or fluoro. For example, in the compounds of formula (I) or in the compounds of formula (IA), it is preferred that q is 1 and $R^1$ is fluoro or that q is 0.

For example, y, z and $R^2$ can be any of the following combinations:
y is 1, z is 1 and both $R^2$ groups are —OH; or
y is 1, z is 1 and each $R^2$ is independently selected from the group consisting of halogen, $C_1$-$C_4$-alkyl, $C_1$-$C_6$-alkoxyl and $C_6$-$C_{10}$-aryloxyl; or
y is 1, z is 2, and $R^2$ is selected from the group consisting of —OH, halogen, $C_1$-$C_4$-alkyl, $C_1$-$C_6$-alkoxyl and $C_6$-$C_{10}$-aryloxyl; or
y is 1, z is 1 and both $R^2$ groups together form a bridging group —O—$(CH_2)_r$—O—, wherein r is 2 or 3, so that the two $R^2$ groups, together with the two oxygen atoms and the boron atom, form a 5- or 6-membered ring, where the $CH_2$ groups are optionally substituted by one or two $C_1$-$C_4$-alkyl groups.

It was specially surprising the fact that the process of the invention provided excellent results when using compounds of formula (II) with many substituents in view of the poor results of 2,6-difluoro and 2,4,6-trifluoro-phenylboronic acids reported by Butchwald et al. Accordingly, it is preferred that p is 2, 3 or 4, and $R^3$ is in each case fluoro or chloro. For example, it is preferred that p is 2 or 3. In a more preferred embodiment p is 2 or 3, $R^3$ is in each case fluoro or chloro, q is 0 or 1, and $R^1$, if present, is fluoro or chloro. Further embodiments of the invention are
p is 0 or 1, $R^3$ is chloro, fluoro or —OH, q is 0 or 1, and $R^1$ fluoro or chloro or —OH;
p is 2 or 3, $R^3$ is in all cases fluoro, and q is 0; or
p is 2 or 3, $R^3$ is in all cases chloro, q is 0 or 1, and $R^1$ fluoro;
each leading to the compounds of formula (IV) used as intermediates in the synthesis of boscalid, fluxapyroxad (or pyraziflumid) and bixafen, respectively.

The compounds of formula (I) and of formula (II) are typically added in equimolar amounts. However, it is possible to use either of them in excess. For example, the compounds of formula (I) or of formula (IA) can be used in excess, as it is typically the most economic reagent. Also, the compounds of formula (IV) or of formula (IVA) may precipitate in the liquid compounds of formula (I), thereby aiding in their isolation and purification. Thus, the compound of formula (I) is preferably used in an amount from 1 to 1.5 equivalents per equivalent of compound (II), for example, in an amount from 1 to 1.3 equivalents per equivalent of compound (II), more preferably in an amount of 1 to 1.2 equivalents per equivalent of compound (II).

Compounds of Formula (V)

The compounds of formula (IV) are key intermediates to the preparation of active ingredients of interest for the agrochemical industry, and the present application therefore is also directed to a process as described in the summary of the invention for the preparation of compounds of formula (V) or a salt thereof.

The process comprises the condensation of a compound to formula (IV) wherein at least one of $R^{11}$ or $R^{12}$ is hydrogen with a compound of formula (VI) Q-C(=O)—Z, comprising the acyl precursor —C(=O)—Z. Acyl precursors that will provide the condensation with the amine group of the compound of formula (IV) are known to the skilled person. This reaction is specifically taught in many documents of the prior art, such as U.S. Pat. No. 8,008,232 or WO 2018/035685 (see page 33).

For example, Z can be selected from the group consisting of —OH, halogen, —$OSO_2R^8$, wherein $R^8$ is $C_1$-$C_{16}$-alkyl, $C_1$-$C_{16}$-haloalkyl or $C_6$-$C_{16}$-aryl optionally substituted with a $C_1$-$C_6$-alkyl group, or a $R^aCOO$— group wherein $R^a$ is $C_1$-$C_6$ alkyl group, where possible, the groups being optionally substituted with one or more halogen atoms. Z is preferably halogen.

Compounds of formula (V) of interest are for example fluxapyroxad and bixafen, wherein Q is 3-(difluoromethyl)-1-methyl-pyrazole-4-carboxyl, or boscalid, wherein Q is 2-chloro-pyridine-3-carboxyl or pyraziflumid wherein Q is 3-trifluoromethylpyrazine-2-carboxyl. Thus, Q is preferably a $C_3$-$C_8$-heteroaryl, preferably comprising a 5 or 6 membered ring having 1 or 2 nitrogen atoms in the ring scaffold. It is thus preferred that Q is selected from the group consisting of pyridine, imidazole, pyrazole, pyrazine, pyrrol, furan, and thiophene, substituted with one or more residues selected from the group consisting of halogen, $C_1$-$C_4$-alkyl and $C_1$-$C_4$ haloalkyl.

Solvent

Suzuki-Miyaura couplings are typically made in water or in a mixture of an organic solvent (e.g. polar protic or aprotic organic solvents) and water.

Polar aprotic solvents are polar solvents without a functional group from which a proton can dissociate. The skilled person is aware of the different polar aprotic solvents available. Examples for suitable polar aprotic solvents are amides, such as N,N-dimethylformamide (DMF) and N,N-dimethylacetamide (DMA); sulfoxides, such as dimethylsulfoxide (DMSO); lactams, such as N-methylpyrrolidone (NMP); cyclic ethers, such as tetrahydrofuran, 1,3-dioxane or 1,4-dioxane; ketones, such as acetone and methylethylketone; nitriles, such as acetonitrile; lactones, such as γ-butyrolactone; nitro compounds, such as nitromethane; ureas, such as tetramethyl urea or dimethylpropylene urea (DMPU); sulfones, such as sulfolan; and carbonic acid esters, such as dimethylcarbonate or ethylenecarbonate.

Polar protic organic solvents suitable for the purposes of the present invention can be alcohols, amines or acids, preferably alcohols such as $C_1$-$C_6$-alcohols, e.g. methanol, ethanol, propanol, isopropyl alcohol (IPA), butanol, t-butanol, sec-butanol, pentanol or hexanol.

Thus, the solvent used in the reaction can be a mixture of water and a polar organic solvent which is at least partially miscible in water, for example a solvent selected from the group consisting of alcohols (preferably, Butanol or IPA, more preferably, butanol), aldehydes (for example, acetaldehyde), ketones (for example, acetone), nitriles (for example, acetonitrile), amides (for example, N,N-dimethylacetamide or DMAc), cyclic ethers (for example, tetrahydrofuran, methyl-tetrahydrofuran, 1,4-dioxane), aromatic amines (for example, pyridine) and mixtures thereof.

When the reaction takes place in the presence of water only it is preferably to add a phase transfer catalyst (PTC). Many are available to the skilled person and non-limitative examples are ammonium salts (e.g. bencyltrialkylammonium halides such as benzyldimethyldecylammonium chloride, or tetraalkylammonium halides such as methyltrioctylammonium chloride, tetrabutyl ammonium bromide (TBAB) or tetrabutyl ammonium iodide (TBAI)), heterocyclic ammonium salts (e.g. 1-butyl-2,3-dimethylimidazolium tetrafluoroborate or Hexadecylpyridinium bromide), non-ionic PTCs (e.g. modified tocopherols such as DL-α-tocopherol methoxypolyethylene glycol succinate) and phosphonium salts (e.g. tetraphenylphosphonium chloride or trihexyltetradecylphosphonium bromide).

The proportion between the organic solvent and water is not particularly relevant and can vary over a wide range. For example, water can form from 0.1 to 90 w/w, or from 0.1 to 70 w/w %, or from 5 to 70 w/w %, or from 10 to 60 w/w %, or from 25 to 80 w/w %, or from 30 to 65 w/w % or from 35 to 60 w/w % or from 45 to 55 w/w % with respect to the total weight of the solvent mixture, the sum of water and organic solvent(s) being 100%.

Base

The Suzuki-Miyaura reaction is carried out in the presence of a base. Suitable bases available to the skilled person are both organic and inorganic bases.

Examples for suitable organic bases are open-chained amines, e.g. trimethylamine, triethylamine, tripropylamine, ethyldiisopropylamine and the like, or basic N-heterocycles, such as morpholine, pyridine, lutidine, DABCO, DBU or DBN.

Inorganic bases are used more frequently and are preferred. Suitable inorganic bases are for example from alkali metal carbonates, e.g. $Li_2CO_3$, $Na_2CO_3$, $K_2CO_3$ or $Cs_2CO_3$, earth alkaline metal carbonates, e.g. $MgCO_3$ or $CaCO_3$, alkali metal phosphates, e.g. $Li_3PO_4$, $Na_3PO_4$, $K_3PO_4$ or $Cs_3PO_4$, earth alkaline metal phosphates, e.g. $Mg_3(PO_4)_2$ or $Ca_3(PO_4)_2$, alkali metal hydrogenphosphates, e.g. $Li_2HPO_4$, $Na_2HPO_4$, $K_2HPO_4$ or $Cs_2HPO_4$, earth alkaline metal hydrogenphosphates, e.g. $MgHPO_4$ or $CaHPO_4$, alkali metal hydroxides, LiOH, NaOH or KOH, and earth alkaline metal hydroxides, e.g. $Mg(OH)_2$ or $Ca(OH)_2$.

It is preferred that the base is an alkali metal carbonate, an alkali metal phosphate or an alkali metal hydrogenphosphate. Even more preferred are alkali metal carbonates, such as $Li_2CO_3$, $Na_2CO_3$, $K_2CO_3$ or $Cs_2CO_3$, $Na_2CO_3$ and $K_2CO_3$ being the most preferred, specially $K_2CO_3$. If conditions could favor the corrosive properties of carbonates, phosphates can be used; for example, $Li_3PO_4$, $Na_3PO_4$, $K_3PO_4$ or $Cs_3PO_4$, preferably $Na_3PO_4$ or $K_3PO_4$.

The base is preferably used in an amount from 0.9 to 10 moles per mol of compound (I), more preferably from 0.9 to 8 moles per mol of compound (I), in particular from 0.9 to 6 moles per mol of compound (I), specifically from 0.9 to 4.4 moles per mol of compound (I), and very specifically from 1 to 4 moles per mol of compound (I), for example from 1 to 3 moles per mol of compound (I).

Reaction Conditions and Purification

The reaction is preferably carried out at a temperature of from 60 to 120° C.; more preferably from 70 to 115° C., in particular of from 80 to 110° C., for example, from 90 to 105° C.

The reaction pressure is not critical. The temperatures used are sometimes higher than the boiling point of at least one of the solvents, and the reaction is then carried out in a closed vessel. This results in an inherent pressure above 1 bar, for example in the range of from 1.1 to 10 bar, in particular from 1.5 to 5 bar, for example from 2 to 4 bar. The reaction is preferably carried out in a pressure vessel, e.g. an autoclave.

The reaction may proceed by adding reagents in different orders, for example, the reaction can be carried out by the standard proceedings for Suzuki-Miyaura reactions. If the catalyst is generated in situ, the Pd source and the ligand of formula (III) can be added first; then the rest of reagents and starting materials are added. But the reaction can also proceed by first mixing the base, the compound of formula (I) and the compound of formula (II), and then adding the catalyst components.

In addition to the order of addition, it is possible to add each of the reagents gradually, especially in the case of a continuous or semi-continuous process, or each one all at once. Also, it is possible to add each component in one portion or in more than one portion. Each of these possibilities can be combined, and for example it is possible to add one reagent in one portion at the beginning of the reaction, and a second reagent in two portions, the first portion being added all at once at the beginning of the reaction, and the second portion being added gradually (e.g. dropwise) after 1, 2, 3, 4, 5 or 6 hours since the reaction reached the desired temperature. For example, the compound of formula (I) and/or the compound (II) can be added in one portion or in more than one portion. In the first case, all the compound of formula (I) and/or the compound (II) is added in one portion. In the second case, in addition to any initial amount, one or more additional portions of compound of formula (I) and/or of compound (II) are added during the reaction, for example, 1, 2, 3, 4, 5 or 6 hours after the reaction has reached the desired temperature. The amounts of each of said portions can be added all at once or gradually (e.g. dropwise).

In an exemplary reaction scheme the palladium source (e.g. palladium chloride or palladium acetate) and the biphenyl phosphine ligand of formula (III) are mixed first in a suitable solvent, stirred, and then mixed with the rest of the reaction components each added all at once in a single portion (base, compound of formula (I) and compound of formula (II)).

However, other combinations are possible, for example the addition of the catalyst components in more than one portion. A first portion of the palladium source (e.g. palladium chloride or palladium acetate) and the biphenyl phosphine ligand of formula (III) can be added and the reaction mixture allowed to react for 1, 2, 3, 4, 5 or 6 hours before adding a second portion of the palladium source (e.g. palladium chloride or palladium acetate) and the biphenyl phosphine ligand of formula (III). Subsequent second, third, fourth or fifth portions of the palladium source (e.g. palladium chloride or palladium acetate) and the biphenyl phosphine ligand of formula (III) can be added. Addition of each portion can proceed all at once or gradually, e.g. dropwise. Thus, the palladium source (e.g. palladium chloride or palladium acetate) and/or the biphenyl phosphine ligand of formula (III) can be added in 1, 2, 3, 4 or 5 portions.

The amounts of the specific reagent in each portion can change. For example, reagents can be added in 2, 3, 4 or 5 portions, each containing 50%, 33%, 25% or 20%, respectively, of the total amount needed to complete the reaction. Each portion does not necessarily include the same amount, and for example a reagent can be added in 2 portions, the first portion comprising 10 to 40% of the total amount added of said reagent, and the second portion can include the rest of the reagent used, that is, 90% to 60%. For example, the compound of formula (II) can be added in 2 portions, the first portion comprising 10% to 40%, preferably 15% to 30%, of the total amount of said reagent added, and the second portion the rest, that is, 90% to 60%, preferably, 85% to 70%. In another example the compound of formula (II) is added in three portions, the first portion comprising 15% to 25% of the total amount of said reagent used, the second portion comprising 15% to 25% the total amount of said reagent used, and the third portion comprising the rest of the of said reagent to reach the total amount used.

In another example the catalyst components are added in 2, 3, 4, 5 or 6 portions. For example, the palladium source and the biphenyl phosphine ligand of formula (III) can each be added in a first portion containing 30% to 70% of the total amount finally used, and after 1, 2, 3, 4 or 5 hours a second portion can be added containing 30% to 70% to complete the total amount finally used of each. In another example the palladium source and the biphenyl phosphine ligand of formula (III) can be added in 2, 3, 4 or 5 portions in each case containing equal or different amounts of each of them. For example, the catalyst components can be added in 3 or 4 portions, each containing 33% or 25%, respectively, of the palladium source and of the biphenyl phosphine ligand of formula (III). The addition regime of each of the components can be combined. For example, the process may comprise first mixing the full amount needed of the base and the compound of formula (I), and a partial amount of the compound of formula (II), for example between 10% and 40% of the total amount finally added. The mixture can then be heated and a first portion of palladium source can be added (for example between 30% and 70% of the total amount finally added), together with a first portion of biphenyl phosphine ligand of formula (III) (for example between 20% and 80% of the total amount finally added). The reaction can be allowed to proceed (for example for less than 1 hour, or 2 hours), and then add dropwise over a period of 1 or two hours the rest of the compound of formula (II). Then, the rest of the palladium source and the biphenyl phosphine ligand of formula (III) can be added in 1, 2 or 3 additional portions.

Another example comprises first adding a first portion of palladium source (for example between 30% and 70% of the total amount finally added), together with a first portion of biphenyl phosphine ligand of formula (III) (for example between 20% and 80% of the total amount finally added). This mixture can then be combined with the full amount needed of the base and the compound of formula (I), and a partial amount of the compound of formula (II), for example between 10% and 40% of the total amount finally added. The mixture can then be heated, and the reaction can be allowed to proceed (for example less than 1 hour, or for 2 hours), and then adding dropwise over a period of 1 or 2 hours the rest of the compound of formula (II). Then, the rest of the palladium source and the biphenyl phosphine ligand of formula (III) can be added in 1, 2 or 3 additional portions.

The addition regime can be simpler by mixing all the reagents together, and then heating the mixture until the reaction has proceeded to an acceptable conversion.

The reaction is preferably carried out in an inert atmosphere to avoid the presence of oxygen, e.g. under an argon or nitrogen atmosphere.

After completion of the reaction, the reaction mixture is worked up and the compound of the formula (IV) is isolated in a customary manner. For example, the solvents are removed, for example under reduced pressure. Preferably, however, the work-up is effected by adding water to the reaction mixture, if desired removing the organic solvent which is at least partially miscible with water, e.g. via distillation, if expedient under reduced pressure, adding a non-polar organic solvent and separating the two phases (aqueous and organic phase).

Non-polar organic solvents are according to the present invention those which have a miscibility with water of below 20 g/100 g of water at 20° C. Examples are aliphatic hydrocarbons, such as alkanes, e.g. pentane, hexane, heptane, octane, mixtures thereof and technical mixtures, such as petrol ether; cycloaliphatic hydrocarbons, such as cycloalkanes, e.g. cyclohexane, cycloheptane, or cyclooctane; chlorinated aliphatic hydrocarbons, such as halogenalkanes, e.g. dichloromethane, trichloromethane, tetrachloromethane, dichloroethane or tetrachloroethane, aromatic hydrocarbons, such as benzene, toluene, the xylenes, ethylbenzene, cumene (isopropylbenzene), chlorobenzene, o-dichlorobenzene or nitrobenzene, open-chained ethers, such as diethylether, dipropylether, methyl-tert-butylether or methyl-isobutylether, and higher alkanols, such as n-butanol or isobutanol. Specifically, a higher alkanol is used.

The compound of formula (IV) is in the organic phase together with the Pd catalyst and the unreacted starting compounds (I) and/or of formula (II), if any. The product of formula (IV) can then be separated from the catalyst and optionally from other undesired components, using routine separation processes. For example, the compound (IV) can be crystallized from the organic phase. Alternatively, the solvent can be removed from the organic phase, e.g. by distillation, e.g. under vacuum, optionally after drying the organic phase, and the solid phase can be taken in another solvent in which the compound (IV) crystallizes better. Exemplary solvents for recrystallization are apolar organic solvents (e.g. hexane, pentane) or alcohols (e.g. propanol, butanol). In yet another alternative, the solid matter is submitted to a chromatographic separation.

EXAMPLES

Example I: Preparation of 3,4,5-Trifluorophenylboronic Acid 27.6 gr (1.14 mol, 1.2 eq) of Magnesium turnings were added to 300 mL Me-THF at room temperature under nitrogen. 200 gr (0.95 mol, 1.0 eq) of 3,4,5-trifluorobromobenzene in 100 ml Me-THF were placed in a dropping funnel. An initial portion of the 3,4,5-trifluorobromobenzene solution in Me-THF (30 ml) was added dropwise with stirring and the initiation of the Grignard reaction was monitored. Once initiated, a spontaneous temperature increase was detected, and turbidity of the reaction solution appeared. Subsequently, all the 3,4,5-trifluorobromobenzene solution was metered in over 3 h. The mixture was stirred at 80° C. for an additional 1 h in order to complete the reaction, and then cooled to room temperature.

A $2^{nd}$ flask was initially charged with a solution of 116.3 mL (1.04 mol, 1.1 eq) trimethyl borate and 200 ml Me-THE, which were precooled to −5° C. Thereafter, the Grignard solution was metered in from the $1^{st}$ flask within 1.5 h. the excess magnesium remained in the 1$^{st}$ flask. Then, the mixture was stirred at room temperature for another 1 h. For hydrolysis: 80 mL of HCl 8% were added dropwise at room temperature and the mixture was stirred for another 1 h. The mixture was heated to 50° C. and the phases were separated. The organic phase was washed with 100 mL water and the aqueous phase was removed again. Subsequently, the organic solvent was evaporated to dryness and the obtained desired solid (156.4 gr, 80.5% purity by assay, 75% yield) was used at the next step without any further purification.

Example II (SPhos, $K_2CO_3$, DMA+$H_2O$) and VI (XPhos, $K_2CO_3$, DMA+$H_2O$)

For Example II 10 mg of palladium chloride (0.057 mmol, 0.05 mol %) and 70 mg of SPhos (0.171 mmol, 0.15 mol %) were dissolved in 40 ml of dimethylacetamide (DMAc): water solution (1:1) at 25° C., under nitrogen and stirred for 15 min to form a catalyst solution.

23.6 g of a potassium carbonate (0.171 mol, 1.5 eq), 20 g of (3,4,5-trifluorophenyl)boronic acid (0.114 mol, 1 eq) and 12 ml of a 2-chloroaniline (0.114 mol, 1 eq) were added to the catalyst solution. 110 ml of additional DMAc:water solution (1:1) were used to transfer the starting materials completely. The reactor was heated to 100° C. inner temperature for 5 h. The reactor was then cooled to 25° C. and the layers were separated.

The organic phase was analyzed by GC area %: 95.6% calculated conversion towards the desired product 3,4,5-trifluoro-2'-aminobiphenyl.

Example VI proceeded in the same way, but substituting SPhos with XPhos, to provide 90% calculated conversion towards the desired product 3,4,5-trifluoro-2'-aminobiphenyl (based on GC area %).

Example III: (SPhos, $K_2CO_3$, IPA+$H_2O$)

4 mg of palladium chloride (0.02 mmol, 0.02 mol %) and 70 mg of SPhos (0.171 mmol, 0.06 mol %) were dissolved in 50 ml of isopropyl alcohol (IPA):water solution (1:1) at 25° C., under nitrogen and stirred for 15 min to form a catalyst solution.

23.6 g of a potassium carbonate (0.171 mol, 1.5 eq), 20 g of a (3,4,5-trifluorophenyl)boronic acid (0.114 mol, 1 eq) and 13.2 ml of a 2-chloroaniline (0.125 mol, 1.1 eq) were added to the catalyst solution. 100 ml of additional IPA: water solution (1:1) were used to transfer the starting materials completely. The reactor was heated to 85° C. inner temperature for 5 h. The reactor was cooled to 25° C. and the layers were separated.

The organic phase was analyzed by GC area %: >99% calculated conversion towards the desired product 3,4,5-trifluoro-2'-aminobiphenyl.

Example IV: (XPhos, $K_3PO_4$, IPA+$H_2O$)

Water and isopropyl alcohol (1:1 mixture) was degassed by sparging with nitrogen for at least 15 min before use. To $PdCl_2$ (0.89 mg, 0.005 mmol, 0.05 mol %), XPhos (7.15 mg, 0.015 mmol, 0.15 mol %) in a 50 mL Schlenk tube under nitrogen with condenser, was added $H_2O$ (10 mL). The resulting mixture was stirred for 30 minutes at 30° C. Then, 2-Chloroaniline (10 mmol, 1 eq), 3,4,5-(Trifluorophenyl) boronic acid (12 mmol, 1.2 eq), $K_3PO_4$ (15 mmol, 1.5 eq) and isopropyl alcohol (10 mL) were added and the resulting mixture was stirred for 16 h at 100° C. After completion of the reaction, the reaction tube was allowed to cool to room temperature and the reaction mixture was extracted with ethyl acetate (3×10 mL, total 30 mL). The organic layers were combined and washed with saturated NaCl (10 mL, NaCl around 3.6 g), dried over $MgSO_4$ (around 1 g), filtered and the organic solvent was evaporated. The reaction mixture was adsorbed onto silica gel, and then purified by column chromatography (petroleum ether/ethyl acetate (10:1)) to afford the desired product (2.07 g, 93%).

Example V: (XPhos, $K_3PO_4$, $H_2O$—Phase Transfer Catalyst)

Water was degassed by sparging with nitrogen for at least 15 min before use. $PdCl_2$ (0.89 mg, 0.005 mmol, 0.05 mol %), XPhos (7.15 mg, 0.015 mmol, 0.15 mol %) and methyltrioctylammonium chloride (4.04 g, 10 mmol, 1 eq) were dissolved in water (10 mL). The resulting solution was stirred at room temperature for 15 minutes before immediate use. The aqueous solution of the catalyst so formed was loaded into a Schlenk tube equipped with a Teflon-coated magnetic stir bar. 2-Chloroaniline (10 mmol, 1 eq), arylboronic acid (12 mmol, 1.2 eq), $K_3PO_4$ (30 mmol, 3 eq) and water (5.0 mL) were added. The tube was evacuated and flushed with nitrogen three times, and then placed in a preheated oil bath (100° C.) for 16 h. After completion of the reaction, the reaction tube was allowed to cool to room temperature and the reaction mixture was extracted with ethylacetate (3×10 mL, total 30 mL). The organic layer was washed with saturated NaCl (10 mL, NaCl around 3.6 g), dried over $MgSO_4$ (around 1 g), filtered and the organic solvent was evaporated. The reaction mixture was adsorbed onto silica gel, and then purified by column chromatography (petroleum ether/ethyl acetate (10:1)) (1.74 g, 78%).

Example VII 28 g of a potassium carbonate (0.203 mol, 1.0 eq), 21.5 ml of a 2-chloroaniline (0.200 mol, 1.0 eq) and 40 g of a (3,4,5-trifluorophenyl)boronic acid (0.223 mol, 1.1 eq) were dissolved in 150 mL of n-butanol and 150 mL of water. 7 mg of palladium chloride (0.041 mmol, 0.02 mol %) and 52 mg of SPhos (0.127 mmol, 0.06 mol %) were added to the reaction mixture without pre-mixing. The reaction was heated to reflux (95-100° C. inner temperature) for 5 h. Upon completion, the reaction was cooled to 25° C. and the layers were separated. The organic phase was analyzed by GC area %: 95.2% calculated conversion towards the desired product 3,4,5-trifluoro-2'-aminobiphenyl.

Example VIII 65 mg of palladium chloride (0.37 mmol, 0.02 mol %) and 0.45 g of SPhos (1.09 mmol, 0.06 mol %) were suspended in 200 ml of n-butanol:water solution (1:1) at 25° C., under nitrogen and stirred for 15 min.

251.4 g of a potassium carbonate (1.82 mol, 1.0 eq), 320 g of a (3,4,5-trifluorophenyl)boronic acid (1.82 mol, 1 eq) and 191.8 ml of a 2-chloroaniline (1.82 mol, 1.1 eq) were added to the catalyst solution. 2.2 L of additional n-butanol: water solution (1:1) were added to consume the starting materials completely. The reaction was heated to reflux (95-100° C. inner temperature) for 5 h. Upon completion, The reaction was cooled to 25° C. and the layers were separated. The organic phase was analyzed by GC area %: 96% calculated conversion towards the desired product 3,4,5-trifluoro-2'-aminobiphenyl.

Example IX 7 mg of palladium chloride (0.041 mmol, 0.02 mol %) and 52 mg of SPhos (0.127 mmol, 0.06 mol %) were suspended in 40 ml of n-butanol:water solution (1:1) at 25° C., under nitrogen and stirred for 15 min.

28 g of a potassium carbonate (0.203 mol, 1.0 eq) and 21.5 ml of a 2-chloroaniline (0.200 mol, 1.0 eq) were dissolved in 50 mL of n-butanol and 130 mL of water. The catalyst suspension was then added at one portion and the reaction was heated to reflux (95-100° C. inner temperature). A solution of 40 g of a (3,4,5-trifluorophenyl)boronic acid (0.223 mol, 1.1 eq) in 80 mL n-butanol was then added dropwise to the reaction mixture during 1 h. The mixture stirred at reflux for 5 h. Upon completion, the reactor was cooled to 25° C. and the layers were separated. The organic phase was analyzed by GC area %: 95.8% calculated conversion towards the desired product 3,4,5-trifluoro-2'-aminobiphenyl.

Example X 4 mg of palladium chloride (0.023 mmol, 0.02 mol %) and 26 mg of SPhos (0.063 mmol, 0.06 mol %) were dissolved in 20 ml of n-butanol:water solution (1:1) at 25° C., under nitrogen and stirred for 15 min.

14.5 g of a potassium carbonate (0.105 mol, 1.0 eq), 21.5 ml of a 2-chloroaniline (0.104 mol, 1.0 eq) and 10 gr solution of (3,4,5-trifluorophenyl)boronic acid in butanol (37.2%, 0.021 mol, 0.22 eq) were dissolved in 30 mL of n-butanol and 65 mL of water. The catalyst suspension was then added at one portion and the reaction was heated to reflux (95-100° C. inner temperature). A solution of 40 g of a (3,4,5-trifluorophenyl)boronic acid (37.2%, 0.848 mol, 0.88 eq) was then added dropwise to the reaction mixture for 1 h. The mixture stirred at reflux for 5 h. Upon completion, the reaction was cooled to 25° C. and the layers were separated. The organic phase was analyzed by GC area %: 98.6% calculated conversion towards the desired product 3,4,5-trifluoro-2'-aminobiphenyl.

Example XI 275 g of a potassium carbonate (1.99 mol, 1.0 eq), 208.3 mL of a 2-chloroaniline (1.99 mol, 1.0 eq) and 350 gr of (3,4,5-trifluorophenyl)boronic acid (1.99 mol, 1.0 eq) were dissolved in 1.14 L of n-butanol and 1.14 L of water. The reaction was heated to reflux (95-100° C. inner temperature). 71 mg of palladium chloride (0.398 mmol, 0.02 mol %) and 490 mg of SPhos (1.19 mmol, 0.06 mol %) were dissolved in 300 ml n-butanol:water (1:1) solution and added to the reaction mixture. The reaction stirred at reflux for 2 h. Then, a second portion of catalyst was added (35.7 mg of palladium chloride (0.2 mmol, 0.01 mol %) and 245 mg of SPhos (0.60 mmol, 0.03 mol %) in 50 mL of n-butanol:water (1:1) solution). The reaction was then stirred at reflux for additional 3 h. Upon completion, the reaction was cooled to 25° C. and the layers were separated. The organic phase was analyzed by GC area %: 93.8% calculated conversion towards the desired product 3,4,5-trifluoro-2'-aminobiphenyl.

Example XII 37.6 mg of palladium chloride (0.21 mmol, 0.02 mol %) and 261 mg of SPhos (0.64 mmol, 0.06 mol %) were dissolved in 200 ml of n-butanol:water solution (1:1) at 25° C., under nitrogen and stirred for 15 min.

146.4 g of a potassium carbonate (1.06 mol, 1.0 eq), 111 ml of a 2-chloroaniline (1.06 mol, 1.0 eq) and 110.4 gr solution of (3,4,5-trifluorophenyl)boronic acid in butanol (37.2%, 0.233 mol, 0.22 eq) were dissolved in 240 mL of n-butanol and 670 mL of water. The catalyst suspension was then added at one portion and the reaction was heated to reflux (95-100° C. inner temperature). A solution of 442 g of a (3,4,5-trifluorophenyl)boronic acid (37.2%, 2.51 mol, 0.88 eq) was then added dropwise to the reaction mixture for 1 h. The mixture stirred at reflux for 5 h. Then, a second portion of catalyst was added 37.6 mg of palladium chloride (0.21 mmol, 0.02 mol %) and 261 mg of SPhos (0.64 mmol, 0.06 mol %) in 100 mL of n-butanol:water (1:1) solution). The reaction was then stirred at reflux for additional 5 h. Upon completion, the reaction was cooled to 25° C. and the layers were separated. The organic phase was analyzed by GC area %: 93.6% calculated conversion towards the desired product 3,4,5-trifluoro-2'-aminobiphenyl.

Example XIII 282.8 g of a potassium carbonate (2.05 mol, 1.0 eq), 214.3 ml of a 2-chloroaniline (2.05 mol, 1.0 eq) and 80 gr of (3,4,5-trifluorophenyl)boronic acid (0.45 mol, 0.22 eq) were dissolved in 0.66 L of n-butanol and 1.3 L of water. The reaction mixture was heated to 95-100° C. inner temperature. One portion of catalyst was prepared: 36 mg of palladium chloride (0.205 mmol, 0.01 mol %) and 250 mg of SPhos (0.610 mmol, 0.03 mol %) in 50 ml n-butanol:water (1:1) solution. The catalyst suspension was then added to the reaction mixture at reflux. Then, 320 gr (3,4,5-trifluorophenyl)boronic acid (0.1.8 mol, 0.88 eq) dissolved in 0.64 L of n-butanol was added dropwise to the reaction during 1 h. The mixture stirred at reflux for 6 h while an additional portion of catalyst (same amount as described above) was added after 1 h, 3 h, 5 h of reflux-total 0.04 mol % catalyst (PdCl2) added. Upon completion, the reaction was cooled to 25° C. and the layers were separated. The organic phase was analyzed by GC area %: 94.4% calculated conversion towards the desired product 3,4,5-trifluoro-2'-aminobiphenyl.

Example XIV 0.45 g of palladium chloride (2.57 mmol, 0.03 mol %) and 3.03 g of SPhos (7.38 mmol, 0.09 mol %) were dissolved in 0.5 L of n-butanol:water solution (1:1) at 25° C., under nitrogen and stirred for 30 min.

1.12 Kg of a potassium carbonate (8.6 mol, 1.02 eq) and 1.032 Kg of a 2-chloroaniline (8.4 mol, 1.0 eq) were dissolved in 4.85 L of water and 1.52 Kg of n-butanol. The reactor was heated to reflux (95-100° C. inner temperature). When the reaction temperature reached 85° C., the catalyst suspension was added and 4 Kg of (3,4,5-trifluorophenyl) boronic acid solution in butanol (61%, 8.6 mol, 1 eq) was added dropwise. After 5 h of reflux, 1.5 gr of palladium chloride (8.46 mmol, 0.1 mol %) and 10 g of SPhos (24.4 mmol, 0.3 mol %) suspended in 200 mL of n-butanol:water (1:1) solution, were added to the reaction mixture, and 0.71 kg of (3,4,5-trifluorophenyl)boronic acid solution in butanol (38%, 1.53 mol, 0.18 eq) were added. The reaction continued to reflux for another 5 h. Upon completion, the reaction cooled to 25° C. and the layers were separated. The organic phase was analyzed by GC area %: 92.7% calculated conversion towards the desired product 3,4,5-trifluoro-2'-aminobiphenyl.

Comparative Examples 1 and 2: $K_2CO_3$, DMA:$H_2O$, AntPhos—Ligand from WO 2018/035685

5.0 mg of palladium chloride (0.028 mmol, 0.05 mol %; comparative example 1) or an equivalent amount of palladium acetate (comparative example 2) and 32 mg of 4-(Anthracen-9-yl)-3-(t-butyl-2,3-dihydrobenzo[d][1,3]oxaphosphole (AntPhos; ligand taught in WO 2018/035685) (0.085 mmol, 0.15 mol %) were dissolved in 20 ml of DMAc:water solution (1:1) at 25° C., under nitrogen and stirred for 15 min to form a catalyst solution.

Then, 11.8 g of a potassium carbonate (0.085 mol, 1.5 eq), 10 g of a (3,4,5-trifluorophenyl)boronic acid (0.057 mol, 1 eq) and 6 ml of a 2-chloroaniline (0.057 mol, 1 eq) were added to the catalyst solution. 55 ml of additional DMAc:water solution (1:1) was used to transfer the starting materials completely. The reactor was heated to 100° C. inner temperature for 5 h. The reactor was cooled to 25° C. and the layers were separated.

The organic phase was analyzed by GC area %: NO conversion towards the desired product (3,4,5-trifluoro-2'-aminobiphenyl) occurred in either case.

Comparative Examples 3 and 4: ($K_2CO_3$, DMAc:$H_2O$, di-t-butylphenylphosphine (dBPP)—Ligand from WO 2018/149813)

5.0 mg of palladium chloride (0.028 mmol, 0.05 mol %; comparative example 3) or an equivalent amount of palladium acetate (comparative example 4) and 19 mg of di-t-butylphenylphosphine (0.085 mmol, 0.015 mol %) taught in WO 2018/149813 were dissolved in 20 ml of DMAc:water solution (1:1) at 25° C., under nitrogen and stirred for 15 min to form a catalyst solution.

Then, 11.8 g of a potassium carbonate (0.085 mol, 1.5 eq), 10 g of a (3,4,5-trifluorophenyl)boronic acid (0.057 mol, 1 eq) and 6 ml of a 2-chloroaniline (0.057 mol, 1 eq) were added to the catalyst solution. 55 ml of additional DMAc:water solution (1:1) were used to transfer the starting materials completely. The reactor was heated to 100° C. inner temperature for 5 h. The reactor was cooled to 25° C. and the layers were separated.

The organic phase was analyzed by GC area %: NO conversion towards the desired product (3,4,5-trifluoro-2'-aminobiphenyl) occurred in either case.

Table 1 below summarizes the experiments:

TABLE 1 summary of experiments

| | Pd (mol %) | Ligand (mol %) | base (eq.) | T (° C.) | solvent | eq-Formula (I) | Yield or Conversion (%) |
|---|---|---|---|---|---|---|---|
| II | $PdCl_2$ (0.05) | SPhos (0.15) | $K_2CO_3$ (1.5) | 100 | DMAc:water (1:1) | 1 | Conversion 95.6 |
| III | $PdCl_2$ (0.02) | SPhos (0.06) | $K_2CO_3$ (1.5) | 85 | IPA:water (1:1) | 1.1 | Conversion >99 |
| IV | $PdCl_2$ (0.05) | Xphos (0.15) | $K_3PO_4$ (1.5) | 100 | IPA:water (1:1) | 0.8 | Yield 93 |
| V | $PdCl_2$ (0.05) | Xphos (0.15) | $K_3PO_4$ (3) | 100 | H2O + PTC (1 eq.) | 0.8 | Yield 78 |
| VI | $PdCl_2$ (0.05) | Xphos (0.15) | $K_2CO_3$ (1.5) | 100 | DMAc:water (1:1) | 1 | Conversion 90 |
| VII | $PdCl_2$ (0.02) | SPhos (0.06) | $K_2CO_3$ (1.0) | 95 | BuOH:water (1:1) | 1 | Conversion 95.2% |
| VIII | $PdCl_2$ (0.02) | SPhos (0.06) | $K_2CO_3$ (1.0) | 95 | BuOH:water (1:1) | 1 | Conversion 96% |
| IX | $PdCl_2$ (0.02) | SPhos (0.06) | $K_2CO_3$ (1.0) | 95 | BuOH:water (1:1) | 1 | Conversion 95.8% |
| X | $PdCl_2$ (0.02) | SPhos (0.06) | $K_2CO_3$ (1.0) | 95 | BuOH:water (1:1) | 1 | Conversion 98.6% |
| XI | $PdCl_2$ (0.03) | SPhos (0.09) | $K_2CO_3$ (1.0) | 95 | BuOH:water (1:1) | 1 | Conversion 93.8% |
| XII | $PdCl_2$ (0.04) | SPhos (0.12) | $K_2CO_3$ (1.0) | 95 | BuOH:water (1:1) | 1 | Conversion 93.6% |
| XIII | $PdCl_2$ (0.04) | SPhos (0.12) | $K_2CO_3$ (1.0) | 95 | BuOH:water (1:1) | 1 | Conversion 94.4% |
| XIV | $PdCl_2$ (0.13) | SPhos (0.39) | $K_2CO_3$ (1.0) | 95 | BuOH:water (1:1) | 1 | Conversion 92.7% |
| comp. 1 | $PdCl_2$ (0.05) | AntPhos (0.15) | $K_2CO_3$ (1.5) | 100 | DMAc:water (1:1) | 1 | No conversion |
| comp. 2 | $Pd(OAc)_2$ (0.05) | AntPhos (0.15) | $K_2CO_3$ (1.5) | 100 | DMAc:water (1:1) | 1 | No conversion |
| comp. 3 | $PdCl_2$ (0.05) | dBPP (0.15) | $K_2CO_3$ (1.5) | 100 | DMAc:water (1:1) | 1 | No conversion |
| comp. 4 | $Pd(OAc)_2$ (0.05) | dBPP (0.15) | $K_2CO_3$ (1.5) | 100 | DMAc:water (1:1) | 1 | No conversion |

The invention claimed is:
1. A process to prepare a compound of formula (IV) or a salt thereof

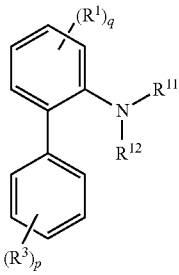

wherein
q is an integer selected from the group consisting of 0, 1, 2, 3 and 4;
p is an integer selected from the group consisting of 1, 2, 3, 4 and 5;
$R^{11}$ is hydrogen or a nitrogen protecting group;
$R^{12}$ is hydrogen;
each $R^1$, if present, is independently selected from the group consisting of the halogens; and
each $R^3$ is independently selected from the group consisting of the halogens;
the process comprising reacting an ortho-substituted aniline and a phenylboro derivative in the presence of a base and a palladium catalyst, said palladium catalyst comprising a palladium source and a biphenyl phosphine ligand,
wherein said ortho-substituted aniline is a compound of formula (I), or a salt thereof

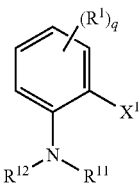

wherein
q, $R^1$, $R^{11}$ and $R^{12}$ are as defined above; and
$X^1$ is a group capable of transmetalation with palladium;
wherein said phenylboro derivative is a compound of formula (II)

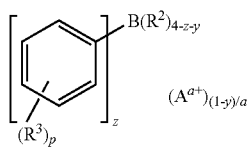

wherein
p and $R^3$ are as defined above;
y is an integer selected from 0 or 1;
wherein,
when y is 1, then z is an integer selected from 1, 2 or 3;
when y is 0, then z is an integer selected from 1, 2, 3 or 4, and the compound of formula (II) forms a borate accompanied by a cation A having a charge a+;
and
each $R^2$ is independently selected from the group consisting of hydrogen, halogen, —OH, —$OR^9$, and $C_1$-$C_{10}$-alkyl, wherein $R^9$ is $C_1$-$C_{10}$-alkyl or $C_6$-$C_{12}$-aryl; or wherein, z being 1, two $R^2$ groups together form a bridging group —O—$(CH_2)_r$—O—, wherein r is 2 or 3, so that said two $R^2$ groups, together with the oxygen atoms and the boron atom, form a 5- or 6-membered ring, where the $CH_2$ groups are optionally substituted by one or two $C_1$-$C_4$-alkyl groups;
and
wherein the biphenyl phosphine ligand is a compound of formula (III) or a salt thereof

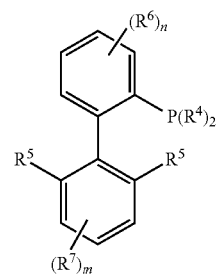

wherein
m is an integer selected from the group consisting of 0, 1, 2 and 3;
n is an integer selected from the group consisting of 0, 1, 2, 3 and 4;
each $R^4$ is independently selected from the group consisting of $C_1$-$C_{16}$-alkyl, $C_3$-$C_{15}$-cycloalkyl, and $C_6$-$C_{10}$-aryl;
each $R^5$ is independently selected from the group consisting of hydrogen, —$OR^{10}$, —$SR_{10}$, —$N(R^{10})(R^{10})$, $C_1$-$C_{16}$-alkyl, $C_3$-$C_{10}$-cycloalkyl, halogen, cyano, and $C_1$-$C_6$-haloalkyl, provided that one $R^5$ is not hydrogen, wherein $R^{10}$ is selected from the group consisting of $C_1$-$C_{16}$-alkyl, $C_3$-$C_{10}$-cycloalkyl, and $C_1$-$C_6$-haloalkyl;
each $R^6$ is independently selected from the group consisting of halogen, cyano, $C_1$-$C_6$-alkyl, $C_1$-$C_6$-haloalkyl, $C_1$-$C_6$-alcoxyl and $C_1$-$C_6$-haloalcoxyl;
each $R^7$ is independently selected from the group consisting of halogen, cyano, $C_1$-$C_6$-alkyl, $C_1$-$C_6$-haloalkyl, $C_1$-$C_6$-alcoxyl and $C_1$-$C_6$-haloalcoxyl.

2. The process according to claim 1, wherein q is 0 or 1.
3. The process according to claim 1, wherein q is not 0.
4. The process according to claim 1, wherein p is 2, 3 or 4, and $R^3$ is in each case fluoro or chloro.
5. The process according to claim 1, wherein p is 2 or 3, $R^3$ is in all cases chloro, q is 0 or 1, and $R^1$, if present, is fluoro.
6. The process according to claim 1, wherein p is 0 or 1, $R^3$, if present, is chloro, fluoro or —OH, q is 0 or 1, and $R^1$, if present, is fluoro, chloro or —OH.
7. The process according to claim 1, wherein $X^1$ is a halogen or —$OSO_2R^8$, wherein $R^8$ is $C_1$-$C_{16}$-alkyl, $C_1$-$C_{16}$-haloalkyl or $C_6$-$C_{16}$-aryl.
8. The process according to claim 1, wherein $X^1$ is chlorine.
9. The process according to claim 1, wherein $R^{11}$ and $R^{12}$ are both hydrogens.
10. The process according to claim 1, wherein $R^4$ is a $C_5$-$C_{15}$-cycloalkyl.

11. The process according to claim 1, wherein both $R^4$ are cyclopentyl, cyclohexyl, cycloheptyl or cyclooctyl.

12. The process according to claim 1, wherein m is 0 or 1.

13. The process according to claim 1, wherein m is 1, and $R^7$ is a $C_1$-$C_6$ alkyl.

14. The process according to claim 1, wherein both $R^5$ are selected from $C_1$-$C_6$-alkyl and $C_1$-$C_6$-alcoxyl.

15. The process according to claim 1, wherein one $R^5$ is hydrogen and the other $R^5$ is selected from the group consisting of $C_1$-$C_6$-alkyl and $C_1$-$C_6$-alcoxyl.

16. The process according to claim 1, wherein n is 0.

17. The process according to claim 1, wherein n is 1, $R^6$ is selected from $C_1$-$C_6$-alkyl and $C_1$-$C_6$-alcoxyl, m is 1 and $R^7$ is selected from $C_1$-$C_6$-alkyl and $C_1$-$C_6$-alcoxyl.

18. A process to produce a compound of formula (V), or a salt thereof,

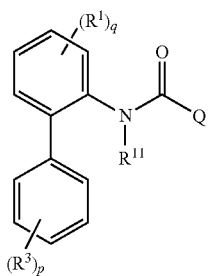

(V)

wherein
q is an integer selected from the group consisting of 0, 1, 2, 3 and 4;
p is an integer selected from the group consisting of 1, 2, 3, 4 and 5;
$R^{11}$ is selected from hydrogen or a nitrogen protecting group;
Q is $C_6$-$C_{15}$-aryl or $C_3$-$C_{15}$-heteroaryl, optionally substituted with one or more groups selected from the group consisting of halogen, $C_1$-$C_4$-alkyl and $C_1$-$C_4$-haloalkyl;
each $R^1$, if present, is independently selected from the group consisting of the halogens; and
each $R^3$ is independently selected from the group consisting of the halogens;
the process comprising preparing
a compound of formula (IV) or a salt thereof according to the process of claim 1; and
the process further comprising,
reacting said compound of formula (IV), or a salt thereof, with a compound of formula (VI)

$$Q\text{-}C(=O)\text{-}Z \qquad \text{formula (VI)}$$

wherein
Q is a defined above; and
—C(=O)—Z is an acyl precursor.

19. The process according to claim 18, wherein said compound of Formula (V) is boscalid, bixafen, pyraziflumid or fluxapyroxad, or a salt thereof.

* * * * *